(12) United States Patent
Smernoff

(10) Patent No.: US 7,918,228 B2
(45) Date of Patent: Apr. 5, 2011

(54) MUSCULOSKELETAL REPOSITIONING DEVICE

(76) Inventor: Gerald N. Smernoff, Annandale, VA (US)

( * ) Notice: Subject to any disclaimer, the term of this patent is extended or adjusted under 35 U.S.C. 154(b) by 288 days.

(21) Appl. No.: 12/254,353

(22) Filed: Oct. 20, 2008

(65) Prior Publication Data
US 2010/0099054 A1 Apr. 22, 2010

(51) Int. Cl.
- A61F 5/37 (2006.01)
- A61F 5/56 (2006.01)
- A61F 11/00 (2006.01)
- A61C 5/14 (2006.01)
- A61C 3/00 (2006.01)
- A61C 19/00 (2006.01)
- A61C 9/00 (2006.01)

(52) U.S. Cl. ........ 128/846; 128/848; 128/857; 128/859; 128/861; 128/862; 433/6; 433/34; 433/36; 433/37; 602/902

(58) Field of Classification Search .......... 128/846, 128/848, 857, 859, 861, 862; 433/6, 34, 433/36, 37; 602/902
See application file for complete search history.

(56) References Cited

U.S. PATENT DOCUMENTS

| | | | | |
|---|---|---|---|---|
| 3,496,936 A | * | 2/1970 | Gores | 128/861 |
| 4,671,766 A | * | 6/1987 | Norton | 433/6 |
| 4,765,324 A | * | 8/1988 | Lake, Jr. | 128/861 |
| 5,042,506 A | * | 8/1991 | Liberati | 128/848 |
| 5,152,301 A | * | 10/1992 | Kittelsen et al. | 128/861 |
| 5,259,762 A | | 11/1993 | Farrell et al. | |
| 5,277,203 A | * | 1/1994 | Hays | 128/861 |
| 5,293,880 A | * | 3/1994 | Levitt | 128/861 |
| 5,339,832 A | | 8/1994 | Kittelsen et al. | |
| 5,611,355 A | * | 3/1997 | Hilsen | 128/848 |
| 5,624,257 A | | 4/1997 | Farrell et al. | |
| 5,718,575 A | | 2/1998 | Cross, III | |
| 5,844,628 A | * | 12/1998 | Hamano et al. | 348/616 |
| 5,865,619 A | | 2/1999 | Cross, III et al. | |
| 5,873,365 A | | 2/1999 | Brown | |
| 5,879,155 A | | 3/1999 | Kittelsen | |
| 6,012,919 A | | 1/2000 | Cross, III et al. | |
| 6,098,627 A | * | 8/2000 | Kellner et al. | 128/859 |
| 6,152,138 A | | 11/2000 | Brown et al. | |
| 6,415,794 B1 | | 7/2002 | Kittelsen et al. | |
| 6,505,626 B2 | | 1/2003 | Kittelsen et al. | |
| 6,505,627 B2 | | 1/2003 | Kittelsen et al. | |
| 6,505,628 B2 | | 1/2003 | Kittelsen et al. | |
| 6,510,853 B1 | | 1/2003 | Kittelsen et al. | |
| 6,530,375 B1 | * | 3/2003 | Cieslik, Jr. | 128/848 |
| 6,588,430 B2 | | 7/2003 | Kittelsen et al. | |
| 6,598,605 B1 | | 7/2003 | Kittelsen et al. | |
| 6,626,180 B1 | | 9/2003 | Kittelsen et al. | |
| 6,675,806 B2 | | 1/2004 | Kittelsen et al. | |
| 6,675,807 B2 | | 1/2004 | Kittelsen et al. | |

(Continued)

Primary Examiner — Patricia M Bianco
Assistant Examiner — Brandon Jackson
(74) Attorney, Agent, or Firm — Blank Rome LLP

(57) ABSTRACT

Musculoskeletal repositioning devices are described. The devices are worn in the mouth and cause the lower jaw of the wearer to move into an active optimal position that relieves stress on the temporomandibular joint, causing increased muscular strength and decreased muscular tension. The devices have ramps on their upper surfaces which contact the upper posterior teeth and lingual anatomy and cause the jaw to reposition from a passive bite position to an active optimal bite position. A casting device for forming a musculoskeletal repositioning device and a method for using the casting device are also described.

17 Claims, 4 Drawing Sheets

U.S. PATENT DOCUMENTS 6,691,710 B2 2/2004 Kittelsen et al.
7,299,804 B2 11/2007 Kittelsen et al.
7,305,990 B2 * 12/2007 Mathias .................. 128/848
7,530,355 B2 * 5/2009 Berghash .................. 128/861
7,549,423 B1 * 6/2009 Hirshberg .................. 128/861
7,637,262 B2 * 12/2009 Bailey .................. 128/848

* cited by examiner

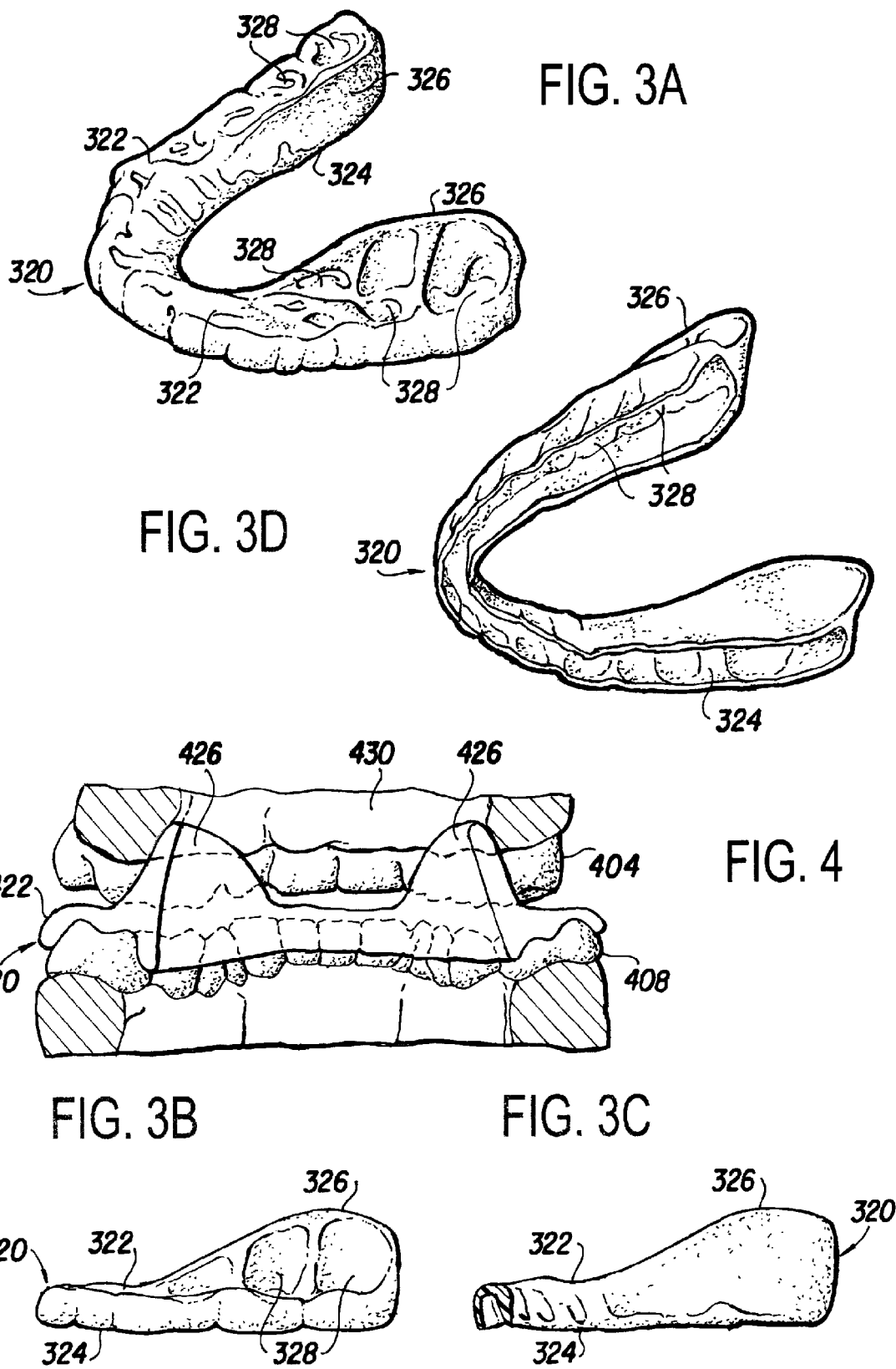

MUSCULOSKELETAL REPOSITIONING DEVICE

FIELD OF THE INVENTION

The present invention relates to musculoskeletal repositioning devices which can aid in athletic performance as well as assist in improving conditions associated with muscular tension. The devices guide the condyles and articulating discs of the temporomandibular joint from a neutral or passive position into an active power position.

BACKGROUND OF THE INVENTION

The temporomandibular joint (TMJ), the joint of the jaw, is a complex joint that must allow for both rotational and translational (sliding) movement. The muscles and joints of the face are thought to be involved in the pathologies of conditions of not just the head and neck, but of the entire body. It has long been considered that tension and improper alignment of the muscles and joints of the face can lead to tension in other parts of the body. As such, oral orthotics and mouthpieces have been developed to try and reduce tension in the facial muscles and joints.

A number of nerves and blood vessels which communicate between the brain and the rest of the body pass through the jaw area near the TMJ. As such, it is thought that abnormalities and stress in this area can cause muscle weakness and muscle tension throughout the body. Further, it is hypothesized that when pressure on the TMJ is released, the energy typically directed towards the masseter muscles can be directed to other parts of the body, improving performance.

A family of patents to Kittelsen, et al., including U.S. Pat. Nos. 7,299,804; 6,691,710; 6,675,807; 6,675,806; 6,626,180; 6,598,605; 6,588,430; 6,510,853; 6,505,628; 6,505,627; 6,505,626; 6,478,492; 6,415,794; 6,012,919; 5,879,155; 5,865,619; 5,339,832; and 5,152,301; describe a mouthpiece made of a thermoplastic material having a "reverse bite plate wedge." The mouthpieces described in the Kittelsen patent are fitted to the upper jaw of the user. As is described in the Kittelsen patents, the mouthpieces are designed to be one-size-fits-all mouthpieces that are fitted to the individual user using a "boil and bite" method wherein the mouthpiece is placed in boiling water to soften the thermoplastic material. According to the Kittelsen patents, the reverse bite plate wedge of the mouthpiece "lowers the condyle from the temporomandibular joint in a fulcrum action." As such, the wedge of the Kittelsen mouthpieces functions to move the condyle downwardly, to open up the TMJ. However, this type of fulcrum action primarily forces the lower jaw to move only downward. Further, as the mouthpieces described by Kittelsen are made of composite layers, they are complicated and expensive to manufacture.

U.S. Pat. Nos. 5,529,762 and 5,624,257 to Farrell describe a mouthguard that receives the teeth of both the upper and lower jaws. The mouthguard has a one-size-fits-all design that is intended to only receive the teeth of both the upper and lower jaws when the lower jaw is in a certain position. As the mouthguards described by Farrell are not custom fitted, they may not move the jaw of the user into the active power position.

As such, there remains a need in the art for devices that can cause the repositioning of the lower jaw to place the TMJ in an active optimal power position for the release of muscular tension and to increase muscular strength.

SUMMARY OF THE INVENTION

It is an object of the present invention to provide musculoskeletal repositioning devices for wearing in the mouth which causes the wearer to have increased muscular strength and decreased muscular tension. The musculoskeletal repositioning devices work by repositioning the jaw into an active optimal position, relieving stress on the temporomandibular joint TMJ.

The musculoskeletal repositioning devices of the present invention have ramps which protrude from the upper surface of the device. The ramps cause the jaws to slide from a neutral or passive bite position to an active optimal bite position when the device is worn. In the active optimal power position the articular disc and the condyle are moved to the active optimal power position from a neutral passive position.

It is a further object of the present invention to provide a casting device which is made up of an upper teeth impression tray and a lower teeth impression tray. The tooth or dental impression trays are positioned relative to one another so that when the user inserts the casting device into his or her mouth, the user's jaw is placed into an active optimal position.

It is a still further object of the present invention to provide methods for forming a musculoskeletal device. A cast of the user's teeth while his or her jaw is in the active optimal position is taken using the casting device of the present invention. The cast taken in this active optimal position can then be used to form a musculoskeletal repositioning device that can be used to reposition the user's jaw into the active optimal power position.

DESCRIPTION OF THE DRAWINGS

Preferred but not limiting embodiments of the invention are set forth in the drawings, in which:

FIG. 3A shows an elevated side view of an embodiment of the musculoskeletal repositioning device of the present invention;

FIG. 3B shows a labial side view of the embodiment of FIG. 3A;

FIG. 3C shows a lingual cross section view of the embodiment of FIG. 3A;

FIG. 3D shows an underneath side view of the embodiment of FIG. 3A;

FIG. 4 shows a back of the mouth or posterior view of a musculoskeletal repositioning device of the present invention while being worn by the user;

DETAILED DESCRIPTION OF THE INVENTION

Embodiments of the present invention are musculoskeletal repositioning devices and methods for making such devices. The devices of the present invention are worn on the teeth of the lower jaw and cause the jaw of the user to move into an active optimal position, relieving tension in the temporomandibular joint and subsequently relieving muscular tension and improving muscular strength throughout the body.

Throughout the specification and drawings, like numbers will refer to like elements with the first number of the reference element referring to the figure in which it is shown. For example, an element with reference number 114 will be referred to as reference number 214 in FIG. 2, and so on.

Figure 1A:
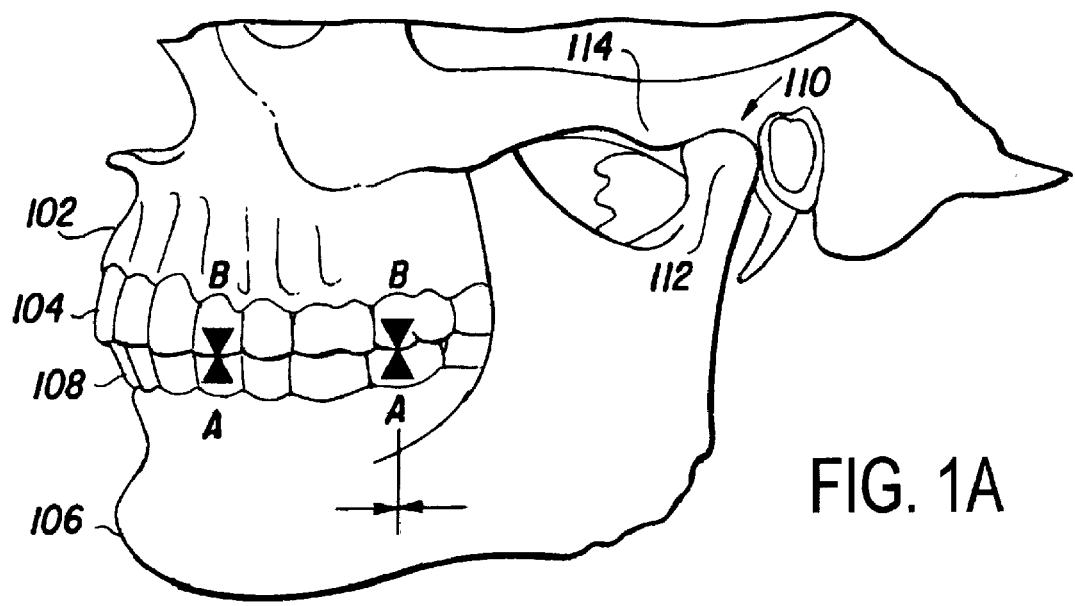
FIG. 1A shows a side view of the human jaw in a normal bite position.

A side view of the human jaw is shown in FIG. 1A. The maxilla 102, or upper jaw bone, is part of the skull and supports the upper teeth 104. The mandible 106, or lower jaw bone, which supports the lower teeth 108, is freely movable and hinges to the skull at the temporomandibular joint (TMJ) 110. The TMJ is a joint connecting the condyle 112 with the temporal bone 114. In most people, the upper teeth 104 and lower teeth 108 normally align in a bite at the arrows A and B as shown in FIG. 1A.

Figure 1B:
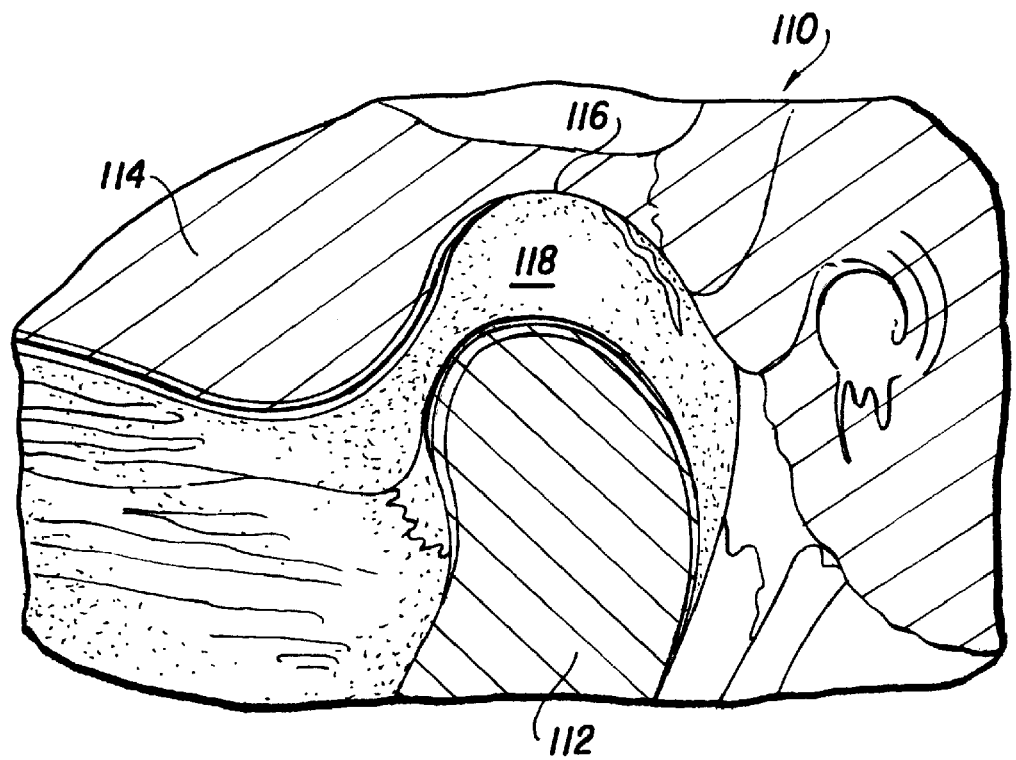
FIG. 1B shows an exploded view of the temporomandibular joint when the jaw is in the neutral or passive position shown in FIG. 1A.

An exploded view of the TMJ 110 when the jaw is in the normally aligned passive position is shown in FIG. 1B. The temporal bone has an articular fossa 116 which typically aligns with the condyle 112. The joint is cushioned by the articulating disk 118, which lies between the temporal bone 114 at the articular fossa 116 and the condyle 112. During athletic activity and other moments of exertion, the clenching of the jaw may increase the pressure exerted on the articulating disc 118. Pressure on the articulating disc 118 in this position can be transferred as stress to the muscles, ligaments, nerves and blood vessels surrounding the TMJ. Because the TMJ is located near nerves and blood vessels that run to and from the brain from the rest of the body, tension in this area is thought to transmit tension to the muscles of the rest of the body.

Figure 2A:
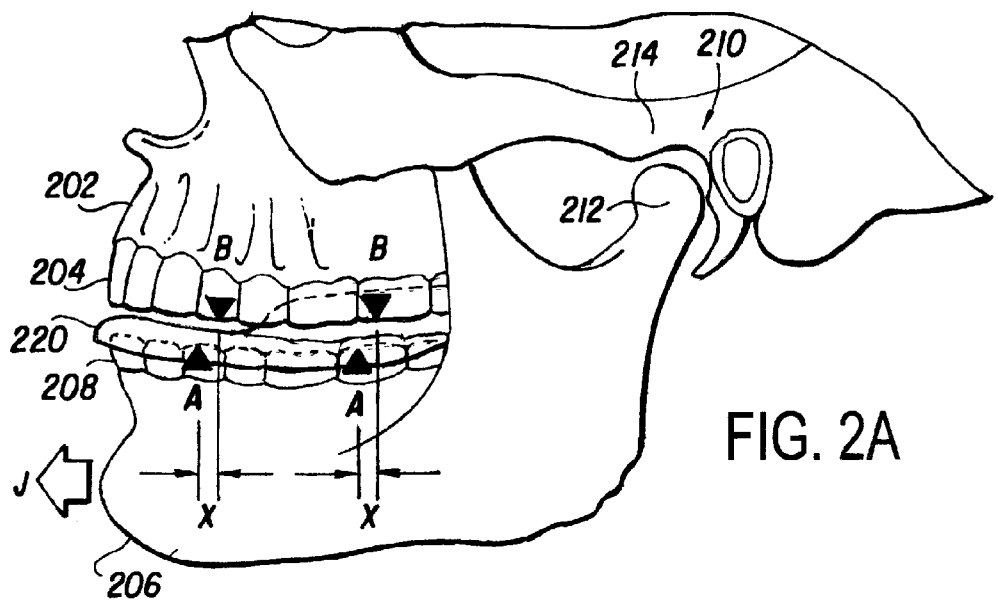
FIG. 2A shows a side view of the human jaw while wearing a musculoskeletal repositioning device of the present invention.
Figure 2B:
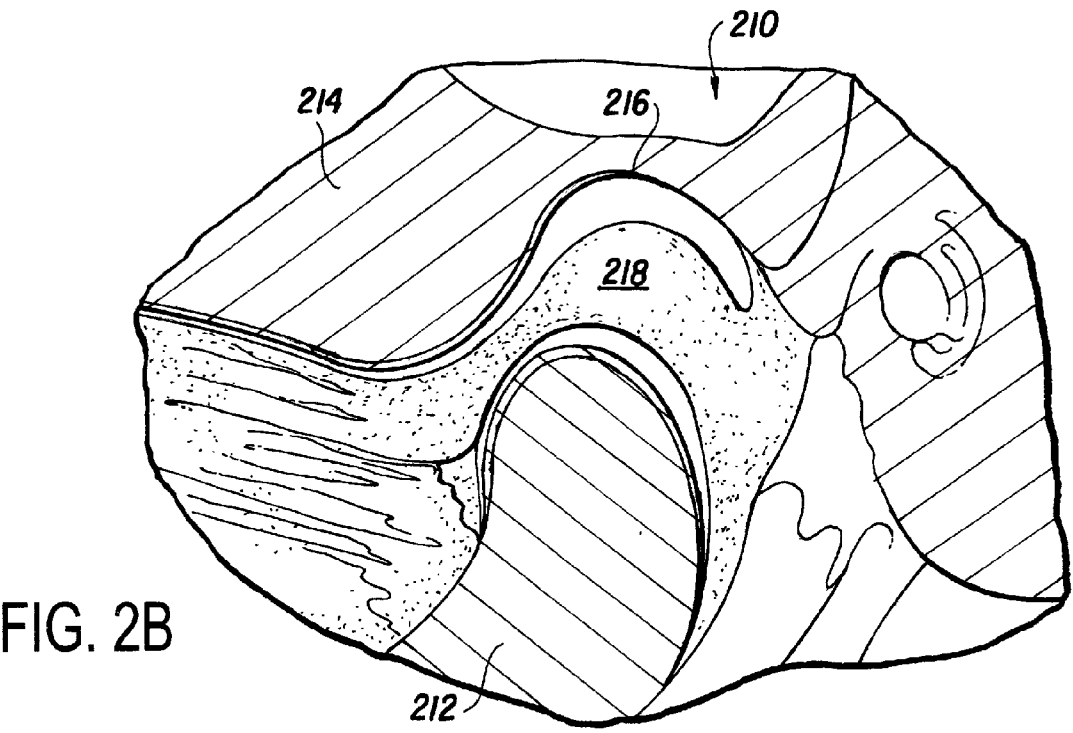
FIG. 2B shows an exploded view of the temporomandibular joint when the jaw is in the active position shown in FIG. 2A.

FIG. 2A shows the human jaw positioned using a musculoskeletal positioning device 220 of the present invention. The device 220, is placed in the mouth on the bottom teeth, causing the lower jaw 206 to move down and forward at the TMJ 210. As is shown in FIG. 2A, the lower jaw 206 moves forward in the direction of arrow J, causing a displacement in the alignment of the upper teeth 204 and lower teeth 208, with the amount of displacement represented by distance X. As is shown in FIG. 2B, this movement of the lower jaw repositions the articular disc 218 into the active or power position in the TMJ 210, allowing for the power that is normally transferred to the jaw joint to be transferred throughout the body, providing the user of the device with increased muscular strength and decreased muscular tension. This position of the jaw may be referred to herein as the active optimal or "power" position.

Turning to FIG. 3, an embodiment of the musculoskeletal devices of the present invention will be described with more detail. In describing the device, terms relative to the positioning of the device in the mouth may be used as are known in the art. For instance, portions of the device which are near or contacting the lips may be referred to as labial portions while portions which are near or contacting the tongue may be referred to as lingual portions. Additionally, portions of the device which lie in the front of the mouth when worn may be referred to as anterior portions while those towards the rear of the mouth may be referred to as posterior portions.

The device 320 show in FIG. 3 is a U-shaped embodiment configured to contact all of the user's posterior teeth. However, it is also contemplated that the device may not be a continuous U-shape but instead may have two separate sections contacting the posterior teeth that are attached to one another with a connector. The connector may be made of the same material as the sections contacting the posterior teeth or may be made of another biocompatible material such as a metal or polymer. In this alternative embodiment, the device may not contact all of the teeth, especially the upper anterior teeth.

The embodiment shown in FIG. 3 has an upper teeth abutment surface 322 for contacting the upper teeth and a lower teeth abutment surface 324 for contacting the lower teeth. The upper teeth abutment surface 322 on each side of the device 320 have ramps 326 which protrude upward from the upper teeth abutment surface 322 on the posterior lingual wall of the device. The ramps 326 of the device 320 cause the lower jaw to move down and forward into the active optimal position when the device is worn.

FIG. 3B shows a labial side view of the device 320, showing how the ramp 326 on the near side of the device 320 protrudes upwardly from the upper teeth abutment surface 322 to include the lingual anatomy. FIG. 3C shows a cross section view of the lingual side of the device 320, showing the lingual side of the opposite ramp 326. FIG. 3D shows an underneath view of the device, more clearly showing the lower teeth abutment surface 324 of this embodiment.

As the devices of the present invention are to be worn on the bottom teeth, the lower teeth abutment surface 324 is typically molded to fit the individual lower teeth. As such, the lower abutment surface 324 usually has tooth indentations 328 to match all or most of the lower teeth which will contact the device 320. In FIG. 3, particularly FIG. 3D, not all of the tooth indentations 328 may be labeled. By contrast, the upper teeth abutment surface 322 may or may not have tooth indentations 328 to match the upper teeth which come in contact with the device 320. In the embodiment shown in FIG. 3, the upper teeth abutment surface only has tooth indentations 328 for the posterior upper teeth, particularly tooth indentations 328 for the upper teeth that contact the ramps 326.

FIG. 4 shows a posterior view of an embodiment of the device 420 in place from the back of the mouth. As can be seen in FIG. 4, the lower teeth abutment surface 424 is molded to fit the lower teeth 408. The ramps 426 contact the posterior upper teeth 404 and the lingual anatomy 430 and cause the lower jaw to move into an active optimal position as is shown in FIG. 2A. In the embodiment shown in FIG. 4, the ramps 426 are high enough to also contact the lingual anatomy 430. However, in other embodiments of the present invention, the ramps 426 may not protrude above the gum line.

Referring to FIGS. 2A, 3 and 4, the ramps of musculoskeletal devices of the present invention cause the user of the device to achieve an active optimal jaw position. The user places the device on the teeth of the lower jaw to hold it in place. When the user then bites down, the upper teeth and/or the lingual anatomy, contact the ramps. The upper teeth and lingual anatomy slide along the ramps into the desired position, transferring the force of the upper teeth and lingual anatomy to the lower teeth abutment surface, causing the lower jaw to move down and forward into the active optimal jaw position. It should also be clear from the description of the device that it will also cause the correct repositioning of the lower jaw even if one or more of the posterior teeth are not present, as the lingual anatomy of the wearer will contact the ramps. This motion repositions the TMJ and hence improves muscular strength and relieves muscular tension. Further, because the ramps cause the repositioning of the lower jaw, the user's jaw will be repositioned whenever they attempt to bite down. The user will not need to be conscious of where their teeth are positioned relative to the device, as the ramps automatically cause their teeth to be positioned correctly.

Figure 5:
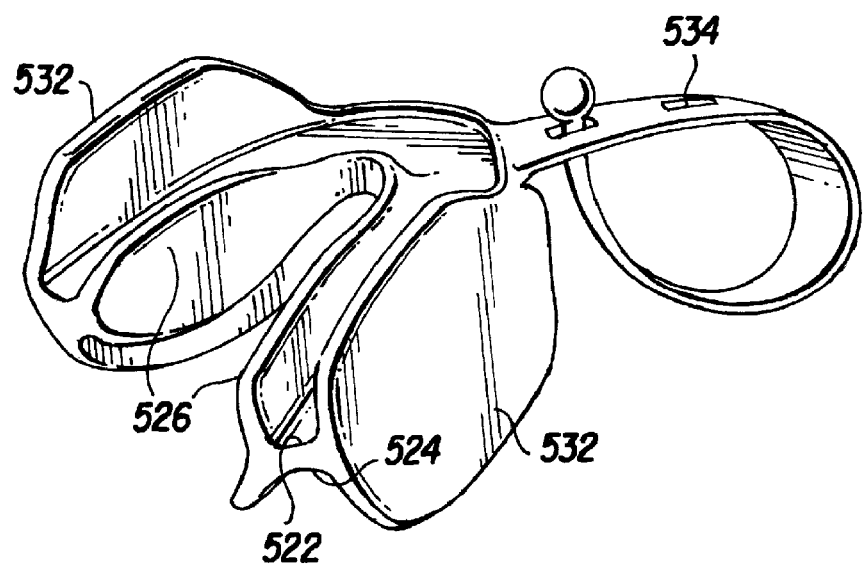
FIG. 5 shows an elevated side view of an embodiment of a musculoskeletal repositioning device of the present invention which also functions as a birthing aid or mouthguard.

FIG. 5 shows an alternative embodiment of the invention, a musculoskeletal repositioning device that has additional protective features allowing it to serve as a birthing aid and a mouthguard as well as enhancing muscular strength and decreasing muscular tension. The embodiment of FIG. 5 has the features of the embodiment of FIG. 3, including an upper teeth abutment surface 522 and a lower teeth abutment surface 524, and ramps 526 for causing the positioning of the lower jaw. Additionally, the embodiment of FIG. 5 has labial protective walls 532, for protecting the teeth and jaw if the mouth of the user would happen to be impacted by an object. The embodiment of FIG. 5 further has an optional strap 534 for attaching the device 526 to a helmet or other headgear.

The devices of the present invention are preferably custom-made made for each user. This may be done using methods known in the art or by methods described below. However, it is also contemplated that the devices of the present invention may be manufactured as one-size-fits-all or in a variety of sizes suitable for consumers.

Figure 6:
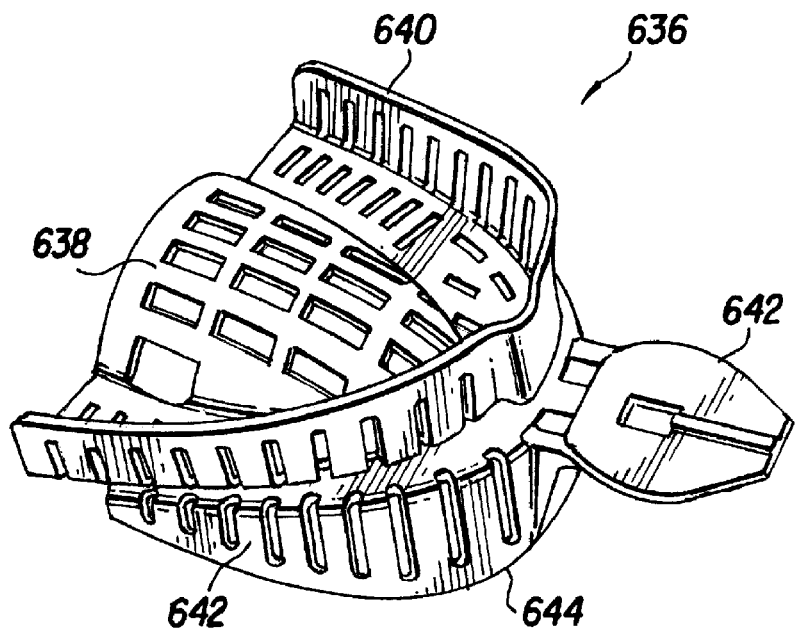
FIG. 6 shows an elevated side view of a casting device of the present invention that can be used to form a musculoskeletal repositioning device.

Also contemplated by the present invention are methods for making custom musculoskeletal repositioning devices. The methods of the present invention involve the use of a casting device 636, as is shown in FIG. 6. The casting device 636 has an upper tooth or dental impression tray 638 having a labial wall 640 fixed to a lower tooth or dental impression tray 642 having a labial wall 644. The two trays are fixed to one another in positions so that when the casting device 636 is used to make a mold of the user's teeth, the user's jaw is placed into the active optimal or power position. The upper teeth impression tray 638 and lower teeth impression tray 642 are positioned so that when the user puts the casting device 636 in his or her mouth and the labial walls 640,644 are held to contact the inside of the user's lips, the lower jaw is moved down and forward into the active optimal position. As the mold of the user's teeth used to create the musculoskeletal device is taken with the jaw in this position, when the device is subsequently worn, the user's jaw will be moved into this active optimal position. The casting device 636 may optionally have a tab 642 that protrudes from the mouth to make it easier to insert and remove the tray.

The casting device 636 can then be used using casting methods well known in the art. Examples of casting methods which may be applied to the present invention include those methods described by Ray R. Padilla, DDS in the CDA Journal, May 2005, Vol. 33, which is hereby incorporated by reference, and those described by commercial labs at www-.precisiondentalworks.com; and www.nightguardlabs.com.

Typically, both the upper teeth impression tray 638 and lower teeth impression tray 642 are filled with a dental casting material. Non-limiting examples of casting materials that may be used with the present invention include Aquasil Easy-Mix Putty, sold by Dentspy Caulk of Milford, Del. and Poly-vinylsiloxane Impression Materials, such as those sold by the Darby Group of Jericho, N.Y. After the trays are filled with casting material, the casting device 636 is placed in the mouth of the user as described above. The casting device is left in the mouth of the user for a sufficient amount of time for the cast to form. After the tray is removed, the cast can then be used to form a mold of the user's teeth. Typically, such molds are made of plaster, but other materials may be used. The mold of the user's teeth can then be used to form a musculoskeletal device that causes the user's jaw to be positioned in an active optimal position when worn. In typical embodiments of the present invention, the cast is sent to a dental professional who forms the dental mold and subsequent musculoskeletal repositioning device.

The musculoskeletal devices of the present invention may be made from any material typically used to make dental mouthpieces, as are well known in the art. In a preferred embodiment, the devices are formed using acrylic. In one embodiment of the present invention, the device is formed using a thermoplastic acrylic for the substructure of the device, a hard non-thermoplastic acrylic for the superstructure and a cushion type or flexible acrylic for the ramps. It is also contemplated that other polymers can be used to form the devices of the present invention, including polyethylenes, vinyl acetates, and styrene. The materials used may be varied depending on the planned use of the device. For constructing a mouthguard such as the embodiment of FIG. 5, softer materials that provide enhanced protection to the teeth and jaw against impacts may be used. The devices of the present invention may be made from one material, may be made from mixtures of materials, or may be made by layering materials.

As is described above, the devices of the present invention cause the repositioning of the lower jaw into an active optimal position, relieving pressure in the TMJ and improving muscular strength while decreasing muscular tension. It should be apparent that the devices of the present invention can be worn during both athletic training and competition. The devices of the present invention may have a handle attached for ease of handling and for attachment to a helmet. The devices of the present invention can be worn during labor as a birthing aid by improving muscular strength while decreasing muscular tension. It is also contemplated that the devices of the present invention can be worn to alleviate symptoms associated with lack of muscular strength and muscle tension. The devices of the present invention may be worn for alleviating problems and discomforts associated with snoring, sleep apnea, sinusitis, childbirth, scoliosis, low back spasms, paraplegic retraining and weak orgasms.

It will be apparent to one of skill in the art that there are other variations of the devices and methods of the present invention that are not explicitly set forth in the specification and drawings that still fall within the scope and spirit of the claims below.

What is claimed is:

1. A musculoskeletal repositioning device for wearing in the mouth, comprising:
   an upper teeth abutment surface for contacting the upper teeth of a user;
   a lower teeth abutment surface for contacting the lower teeth of a user; and
   a ramp protruding upwardly from the upper teeth abutment surface and molded to fit the upper posterior teeth and lingual anatomy of the user; wherein when upper posterior teeth and lingual anatomy contact the ramp, the force exerted by the upper posterior teeth and lingual anatomy on the ramp causes the lower jaw to move downwardly and forwardly into an active optimal position.

2. The musculoskeletal repositioning device of claim 1, wherein the device is formed from acrylic.

3. The musculoskeletal repositioning device of claim 2, wherein the device has an inner layer formed from a thermoplastic acrylic and an outer layer formed from a non-thermoplastic acrylic.

4. The musculoskeletal repositioning device of claim 2, wherein the ramp is formed from a flexible acrylic.

5. The musculoskeletal repositioning device of claim 1, wherein the upper teeth abutment has a posterior edge and wherein the ramp increases in height towards the posterior edge.

6. The musculoskeletal repositioning device of claim 1, wherein the device is formed from a polymer.

7. The musculoskeletal repositioning device of claim 1, wherein the lower teeth abutment surface is molded to fit the lower teeth of the user.

8. The musculoskeletal repositioning device of claim 1, wherein the ramp is molded to fit the upper posterior teeth and lingual anatomy of the user.

9. A musculoskeletal repositioning device for wearing in the mouth, comprising:
- an upper teeth abutment surface and molded to fit the upper posterior teeth and lingual anatomy of a user, the upper teeth abutment surface having a lingual edge, a labial edge and a posterior edge;
- a lower teeth abutment surface for contacting the lower teeth of the user, the lower teeth abutment surface having a lingual edge, a labial edge and a posterior edge; and
- a ramp protruding upwardly from the lingual edge of the upper teeth abutment surface in a direction perpendicular to the upper teeth abutment surface; wherein when molded to fit the upper posterior teeth and lingual anatomy contact the ramp, the force exerted by the upper posterior teeth and lingual anatomy on the ramp causes the lower jaw to move downwardly and forwardly into an active optimal position.

10. The musculoskeletal repositioning device of claim 9, wherein the device is formed from acrylic.

11. The musculoskeletal repositioning device of claim 10, wherein the device has an inner layer formed from a thermoplastic acrylic and an outer layer formed from a non-thermoplastic acrylic.

12. The musculoskeletal repositioning device of claim 9, wherein the ramp increases in height towards the posterior edge.

13. The musculoskeletal repositioning device of claim 9, wherein the device is formed from polymer.

14. The musculoskeletal repositioning device of claim 9, wherein the ramp is formed from a flexible acrylic.

15. The musculoskeletal repositioning device of claim 9, wherein the lower teeth abutment surface is molded to fit the lower teeth of the user.

16. The musculoskeletal repositioning device of claim 9, wherein the ramp is molded to fit the upper posterior teeth and lingual anatomy of the user.

17. A method for forming a musculoskeletal repositioning device comprising:
- providing a casting device for insertion into the mouth having an upper teeth impression tray with a labial wall and a lower teeth impression tray with a labial wall; the teeth impression trays fixed in positions relative to one another so that when a user inserts the casting tray into the mouth, the user's jaw is repositioned into an active optimal position;
- filling the teeth impression trays with a casting material;
- inserting the casting device into the user's mouth;
- obtaining a cast of the user's upper and lower teeth;
- forming a mold from the cast of the user's upper and lower teeth; and
- using the mold to form a musculoskeletal repositioning device fitted to the lower teeth and having a ramp protruding upward from the abutment surface and molded to fit the upper posterior teeth and the lingual anatomy; wherein when the musculoskeletal repositioning device is worn in the mouth of the user, the user's jaw is placed in an active optimal position.

* * * * *